(12) United States Patent
Nakajima et al.

(10) Patent No.: US 8,257,974 B2
(45) Date of Patent: Sep. 4, 2012

(54) METHOD OF REACTION IN FLOW CHANNEL OF MICROCHIP AND ANALYSIS DEVICE

(75) Inventors: Akihisa Nakajima, Tama (JP); Kusunoki Higashino, Osaka (JP); Yasuhiro Sando, Amagasaki (JP); Youichi Aoki, Hachioji (JP); Kohsuke Tanimoto, Kashiwa (JP)

(73) Assignee: Konica Minolta Medical & Graphic, Inc., Hino-Shi (JP)

( * ) Notice: Subject to any disclaimer, the term of this patent is extended or adjusted under 35 U.S.C. 154(b) by 105 days.

(21) Appl. No.: 12/803,060

(22) Filed: Jun. 18, 2010

(65) Prior Publication Data

US 2010/0261290 A1 Oct. 14, 2010

Related U.S. Application Data

(62) Division of application No. 12/225,598, filed as application No. PCT/JP2007/053163 on Feb. 21, 2007, now abandoned.

(30) Foreign Application Priority Data

Mar. 29, 2006 (JP) .................................. 2006-092295

(51) Int. Cl.
*G01N 15/06* (2006.01)
*G01N 33/00* (2006.01)
*G01N 33/48* (2006.01)

(52) U.S. Cl. ............ 436/43; 422/50; 422/68.1; 422/502; 422/503; 422/504; 422/505; 422/506; 422/507; 422/129; 436/63; 436/174; 436/177; 436/178; 436/180

(58) Field of Classification Search .................... 422/50, 422/68.1, 502, 503, 504, 505, 506, 507, 129; 436/43, 63, 174, 177, 178, 179, 180
See application file for complete search history.

(56) References Cited

U.S. PATENT DOCUMENTS 6,132,685 A 10/2000 Kercso et al.
(Continued)

FOREIGN PATENT DOCUMENTS

JP 2001-322099 A 11/2001
(Continued)

OTHER PUBLICATIONS

Japanese Office Action dated Jan. 10, 2012 (and English translation thereof) in counterpart Japanese Application No. 2008-511983.
(Continued)

*Primary Examiner* — Brian J Sines
(74) *Attorney, Agent, or Firm* — Holtz, Holtz, Goodman & Chick, PC (57) ABSTRACT

In the case of passing a reagent in a reaction channel in a microchip, which carries a reactant capable of reacting with the reagent on the wall thereof, and bringing the reactant into contact with the reagent so as to carry out a reaction, the reagent is efficiently passed to the reactant to thereby promote the progress of the reaction. In carrying out the reaction as described above, the reagent (30a) is passed in such a manner that the periphery of the gas/liquid interface at the front end of the reagent moves forward and backward along the wall face of the reaction channel (10). After the completion of the reaction between the reagent (30a) and the reactant, another reagent (30b), which is to be reacted with the reactant capable of reacting with the reagent that is carried on the reaction channel, is passed into the reaction channel (10) while providing a gas in the front edge side thereof. In carrying out the reaction, the reagent (30b) is passed in such manner that the periphery of the gas/liquid interface at the front end of the reagent moves forward and backward along the wall face of the reaction channel (10).

7 Claims, 8 Drawing Sheets

U.S. PATENT DOCUMENTS

| | | |
|---|---|---|
| 6,358,387 B1 | 3/2002 | Kopf-Sill et al. |
| 6,803,568 B2 | 10/2004 | Bousse et al. |
| 6,877,892 B2 * | 4/2005 | Karp .................. 366/341 |
| 6,890,093 B2 * | 5/2005 | Karp et al. ............ 366/336 |
| 6,966,880 B2 | 11/2005 | Boecker et al. |
| 6,990,851 B2 | 1/2006 | Spaid et al. |
| 7,148,476 B2 | 12/2006 | Andersson et al. |
| 7,261,858 B2 | 8/2007 | Agren |
| 2002/0058329 A1 | 5/2002 | Singh et al. |
| 2004/0019313 A1 | 1/2004 | Childers et al. |
| 2004/0086427 A1 | 5/2004 | Childers et al. |
| 2004/0091398 A1 | 5/2004 | Gilbert et al. |
| 2005/0279925 A1 | 12/2005 | Andersson et al. |
| 2006/0046300 A1 | 3/2006 | Padmanabhan et al. |

FOREIGN PATENT DOCUMENTS

| | | |
|---|---|---|
| JP | 2003-098175 A | 4/2003 |
| JP | 2004-108285 A | 4/2004 |
| JP | 2004-270537 A | 9/2004 |
| JP | 2005-134372 A | 5/2005 |
| JP | 2005-323519 A | 11/2005 |
| WO | WO 03/000416 A2 | 1/2003 |
| WO | WO 2005/108571 A1 | 11/2005 |

OTHER PUBLICATIONS

Extended European Search Report (EESR) dated Feb. 22, 2012 (in English) in counterpart European Application No. 07714663.7.

* cited by examiner

METHOD OF REACTION IN FLOW CHANNEL OF MICROCHIP AND ANALYSIS DEVICE

CROSS-REFERENCE TO RELATED APPLICATION

This application is a Divisional application of application Ser. No. 12/225,598 filed Sep. 25, 2008, now abandoned which is a US National Phase (35 USC 371) of PCT/JP2007/053163 filed Feb. 21, 2007, which is incorporated herein in its entirety by this reference.

TECHNICAL FIELD

The present invention relates to a method of reaction in a flow channel of microchip and an analysis device. More specifically the present invention relates to a method of reaction between a reacting material carried on an inner surface of the wall of the flow channel (simply called reacting material hereinafter) and the reagent in the flow channel by flowing the reagent into the flow channel and contacting the reagent with the reacting material and related to an analysis device.

BACKGROUND ART

In recent years, due to the use of micro-machine technology and microscopic processing technology, systems are being developed in which devices and means (for example pumps, valves, flow channels, sensors and the like) for performing conventional sample preparation, chemical analysis, chemical synthesis and the like are miniaturized and integrated on a single chip (Patent Document 1). These systems are called μ-TAS (Micro Total Analysis System), bioreactor, lab-on-chips, and biochips, and are much expected to be applied in the fields of medical testing and diagnosis, environmental measurement and agricultural manufacturing.

The quantitative performance of analysis, accuracy of analysis and economic efficiency in these types of analysis and testing are considered important when using these types of chips for analysis. (These types of chips which have micro flow channels and in which various reactions are performed in the micro flow channels are called microchips.) As a result, it is an issue to provide a feeding system which has a simple structure and is highly reliable. A micro fluid control device which has high accuracy and excellent reliability is required. Micro-pump systems and control methods which meet this need have already been proposed. (Patent Documents 2-4)

Patent Document 1: Unexamined Japanese Patent Application No. 2005-323519
Patent Document 2: Unexamined Japanese Patent Application No. 2001-322099
Patent Document 3: Unexamined Japanese Patent Application No. 2004-108285
Patent Document 4: Unexamined Japanese Patent Application No. 2004-270537

DISCLOSURES OF THE INVENTION

Problems to be Solved by the Invention

The inventors Of the present invention have been studying on microchips for performing amplification and detection of specific genes in a specimen with high sensitivity. In this type of microchip, in some cases the reacting material is carried on the wall surface of the flow channel inside the chip and a reaction is performed when a plurality of reagents are flowed in sequence into the flow channel, thereby bringing sequentially the reagents in contact with the reacting material carried.

More specifically, for example, gene amplification is performed in the flow channel of the microchip using biotinylated primer; then the amplified gene is denatured to form a single strand and is fed into a flow channel for detection in which a biotin affinity protein such as streptavidin is absorbed and fixed onto the wall formed of polystyrene and the like; then the gene is fixed on the wall of the flow channel by the bonding reaction of biotin affinity protein and the biotin; then a probe DNA whose end has been fluorescently labelled with FITC (fluorescein isothiocyanate) is flowed into the flow channel and hybridized with the fixed gene; then the gold colloid whose surface has been modified with an FITC antibody which bonds specifically with FITC is flowed into the flow channels; and then the gold colloid is adsorbed by the FITC modified probe that has been hybridized with the gene. The amplified gene is detected high-sensitively by optically measuring the concentration of the adsorbed gold colloid.

In the micro flow channel formed in a substrate of the microchip, a flow velocity in fluid flow forms a gradient in the direction perpendicular to the flow channel and the flow velocity decreases as approaching to the wall surface of the flow channel. In the vicinity of the wall surface of the flow channel, the fluid flow velocity is substantially 0. As a result, when the reaction is to be performed by flowing a reagent into the flow channel in which the reacting material is carried on the wall surface of the flow channel as in the case above, even when the reagent is flowed into the flow channel, the reagent stays at the wall surface vicinity and does not flow and thus it is difficult to continue supplying reagent to reacting material such as the amplified gene carried on the wall surface of the flow channel and the reaction does not progress. Even in the case where other reagents are successively forced into the flow channel to carry out the reaction, when the different fluids including the various reagents are flowed continuously, a portion of the previous fluid remains on the wall surface and because the previous fluid is not replaced with the next fluid, the reaction does not progress.

It is to be noted that Patent Document 1 discloses technology in which in a micro fluid device for testing a reagent by flowing the reagent into the flow channel formed in a chip and gas in injected between the reagent and the drive fluid for pushing and sending the reagent driven by the micropump from the upstream side such that the reagent and the drive fluid do not come indirect contact with each other. However, the technology disclosed in this document causes reduction in the amount of reagent due to the placement of gas between the reagent and the driving fluid, but there is no mention about the present invention.

The object of the present invention is to speed up the progress of the reaction by allowing efficient flow of the reagent into the reacting material when the reacting material and the reagent are brought in contact with each other and react by flowing the reagent into the reaction flow channel in which the reacting material is carried on the wall surface of the flow channel formed in a substrate of the microchip.

Means for Solving the Problem

The method of reaction of microchip in a flow channel disclosed in the present invention is a reaction method in which a reaction is performed by bringing the reagent in contact with the reaction by flowing the reagent into the reaction flow channel in which the reacting material which reacts with the reagent is carried on the wall surface of the flow channel of the microchip, wherein the reagent is fed such that at the time when the reaction is performed, the peripheral portion of the gas-liquid interface in the front end of the reagent moves back and forth on the wall surface of the reaction flow channel.

In a preferable aspect of the invention above, when the reaction is performed, an operation of flowing the reagent is performed at least once such that the peripheral portion of the gas-liquid interface in the front end of the reagent passes in the forward direction on the wall surface of the reaction flow channel, then the peripheral portion passes in the reverse direction on the wall surface of the reaction flow channel after reaching to a flow channel ahead of the reaction flow channel, and then the peripheral portion once again passes in the forward direction on the wall surface of the reaction flow channel.

Furthermore, in the method of reaction of microchip in a flow channel disclosed in the present invention, after the reaction between the reagent and the reacting material is performed, the other reagent that reacts with the reacting material carried in the reaction flow channel is flowed into the reaction flow channel through the intervening gas space at the front end side of the reacting material, such that, when the reaction of other reagent is performed, the peripheral portion of the gas-liquid interface at the front end of the other reagent moves back and forth on the wall surface of the reaction flow channel.

In a preferable aspect of the above invention, when the reaction between the other reagent and the reacting material is performed, an operation is performed at least once, such that the peripheral portion of the gas-liquid interface at the front end of the other reagent passes on the wall surface of the reaction flow channel in the forward direction, then the peripheral portion passes in the reverse direction on the wall surface of the reaction flow channel after reaching to a flow channel ahead of the reaction flow channel, and then the peripheral portion once again passes in the forward direction on the wall surface of the reaction flow channel.

In another preferable aspect of this invention, the microchip comprises:

a reagent holding flow channel in which the other reagent is stored;

a gas storage flow channel which is disposed at the downstream side of the reagent holding flow channel and communicates directly or indirectly with the reaction flow channel at the downstream side;

a water repellent valve which is arranged between the downstream end of the reagent holding flow channel and the upstream end of the gas storage flow channel and includes a feed control flow channel that has a smaller cross-sectional area than these flow channels and which passes the other reagent forward from the reagent holding flow channel by applying fluid flow pressures larger than a predetermined pressure from the upstream side; wherein after the reaction between the reagent and the reacting material is performed, the other reagent stored in the reagent holding flow channel is pushed to the front from the reagent holding flow channel through the water repellent valve and the other reagent is fed into the reaction flow channel through the intervening gas space at the front end of the other reagent, and is flowed such that the peripheral portion of the gas-liquid interface at the front side of the other reagent moves back and forth on the wall surface of the reaction flow channel to react the other reagent with the reacting material.

In the invention above, the flow channel ahead of the reaction flow channel forms a closed air tight space. It is preferred that the peripheral portion of the gas-liquid interface at the front end of the reagent moves back and forth on the wall surface of the reaction flow channel by reducing the pressure after the reagent is flowed into reaction flow channel by pressure from the outside.

In this case, the volume of the closed flow channel ahead of the reaction flow channel is preferably larger than the volume of the reaction flow channel.

Furthermore, it is preferable to provide a gas vent channel which has an end which is opened to an outer atmosphere is provided at a position before the reaction flow channel.

The analysis device of the present invention to which is loaded a microchip which includes a reaction flow channel in which a reacting material which reacts with a reagent is carried on the wall surface of the flow channels, and in which a reaction is performed by feeding the reagent into reaction flow channel and bring the reagent in contact with the reacting material;

and the analysis device comprises a feeding means which flows the reagent such that, when the reaction is performed, the peripheral portion of the gas-liquid interface at the front end of the other reagent moves back and forth on the wall surface of the reaction flow channel.

According to the present invention, the meniscus is moved back and forth on the wall surface of the reaction flow channel in which the reacting material that reacts with the reagent is carried, and thus separation of the reagent from the wall surface as well as new contact of the reagent with the wall surface progresses due to multiple passages of the gas-liquid interface, and substitution of the reagent on the wall surface of the flow channel is effectively performed and thus reaction progress is sped up.

By configuring the flow channel ahead of the reaction flow channel as a closed air tight flow channel, the reagent is flowed by pressure into the reaction flow channel, then the reagent is pushed back to the reaction flow channel as the gas space in the closed flow channel has been compressed by the reagent when the liquid feed pressure is released, and in this manner, the reagent is caused to move back and forth.

Effects of the Invention

According to the present invention, the reagent effectively circulates to the reacting material which reacts with the reagent and is carried on the wall surface of the flow channel of the microchip, and the progress of the reaction can be sped up.

DESCRIPTION OF REFERENCE NUMERALS

1 Microchip
2 Analysis device
10 Reaction flow channel
10a Wall surface
21 Flow channel
22 Flow channel
30a First reagent
30b Second reagent
30c Third reagent
31 Front end of reagent (Gas-liquid interface)
35 Drive fluid
40a, 40b Reagent holding flow channel
50a, 50b Gas storage flow channel
60 Water repellent valve
61 Feed control channel
62a, 62b Flow channel
63 Fluid
71 First reagent flow channel
72 Common flow channel
81a, 81b Drive fluid injection port
82a, 82b Drive fluid flow channel
83a, 83b Gas vent channel Preferable Embodiments of the Invention Embodiments of the present invention will be described in the following with reference to the drawings. In the microchip used in the present invention, with the aims of various tests, chemical analysis, chemical synthesis, sample processing and separation, reactions using reagents are performed on the micro flow channels provided inside the plate-like chip.

In the present invention, the application of the microchip includes biological testing and analysis by gene amplification reaction and antigen-antibody reaction. The invention is also used for chemical testing and analysis, chemical synthesis of target compound by organic synthesis, drug screening, drug effect screening, drug extraction and formation and separation of metal complexes.

Figure 1:
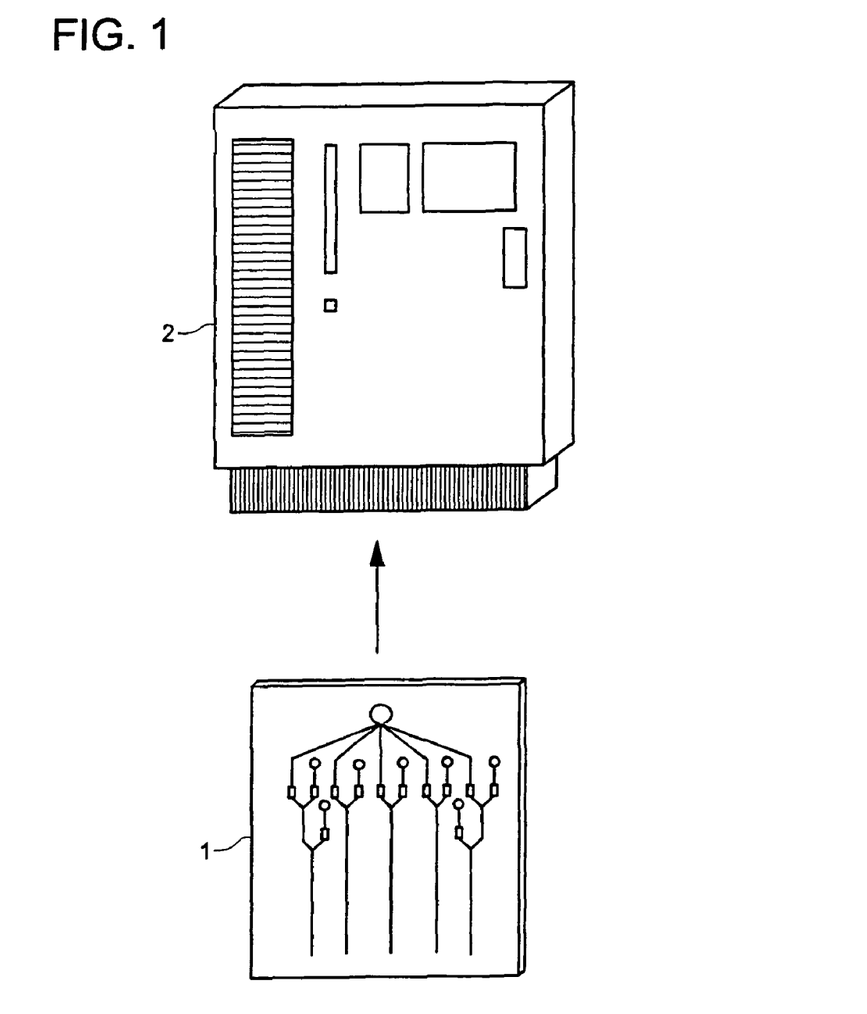
FIG. 1 shows an example of the overall structure of microchip used in the present invention and the control device thereof.

In the following embodiment, the example is given in which a specimen is injected into the flow channel formed in the microchip and mixed with the amplification reagent in the flow channel to perform gene amplification, then the amplified gene is fixed and detected in the downstream flow channel. As shown in FIG. 1, the microchip it a plate shaped chip that is made of a material such as resin and micro flow channels are provided inside the chip. Various fluids such as reagents are flowed into the injection port provided at the upstream side of the microchip 1 by injecting drive fluid that is driven by liquid flowing means such as an independent drive pump, and by moving the drive fluid in the forward and reverse direction by a micropump. The microchip 1, the temperature control device, the optical detection device and the like are incorporated into the analysis device 2, and by loading the microchip 1 into the analysis device 2, the series of analysis operation can be performed automatically.

After the microchip 1 is loaded into the analysis device 2, the biotin modified primer is used to amplify the gene in the flow channel of the microchip 1 and the amplified gene is denatured to form a single strand. The resultant solution (called first reagent hereinafter) is flowed into the flow channel on the wall of which a biotinophilic protein such as streptavidin is carried and fixed. The gene is fixed in the wall of the flow channel due to the bonding reaction between the biotinophilic protein and the biotin.

Next, a probe DNA (called second reagent hereinafter) whose end has been fluorescently labelled with FITC is flowed into the flow channel and hybridized with the fixed gene.

The solution of the gold colloid (called third reagent hereinafter) whose surface has been modified with an anti-FITC antibody which bonds specifically with FITC flowed into the flow channels and the gold colloid is adsorbed to the FITC modified probe that has been hybridized with the gene. The amplified gene is detected by optically measuring the concentration of the adsorbed gold colloid.

It is to be noted that the reacting material in the description below that is carried in the flow channel wall refers to the biotinophilic protein, the gene that has bonded with the biotinophilic protein, or the DNA probe that has been hybridized with the gene.

First Embodiment

FIG. 2-FIG. 5 are explanatory drawings for the flowing of the first reagent into the reaction flow channel in which the reacting material is carried in the first embodiment of this invention. In these drawings, 10 denotes the reaction flow channel that has the reacting material carried on its wall surface. By flowing the first reagent 30a into the reaction flow channel 10, the first reagent 30a is brought in contact with the reacting material and the reaction is performed.

Figure 2:
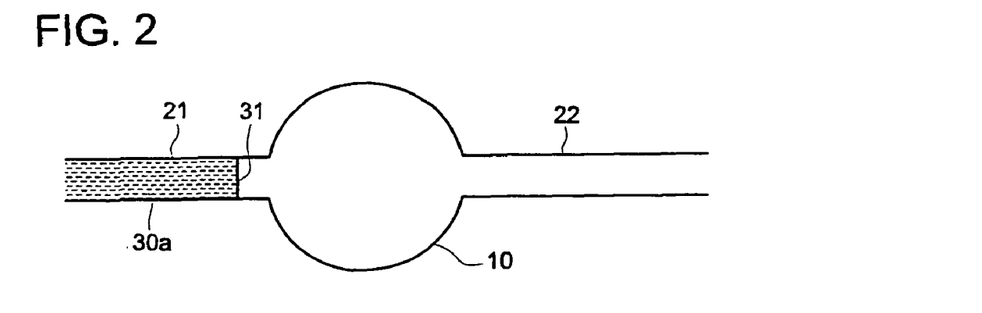
FIG. 2 is an explanatory drawing for the flowing of the first reagent into the reaction flow channel in which the reacting material is carried in the first embodiment of this invention

The operation of feeding the first reagent 30a at the time of reaction will be described sequentially in the following. First as shown in FIG. 2, the first reagent 30a is supplied to the reaction flow channel 10 through the upstream flow channel 21 of the reaction flow channel 10.

Figure 3:
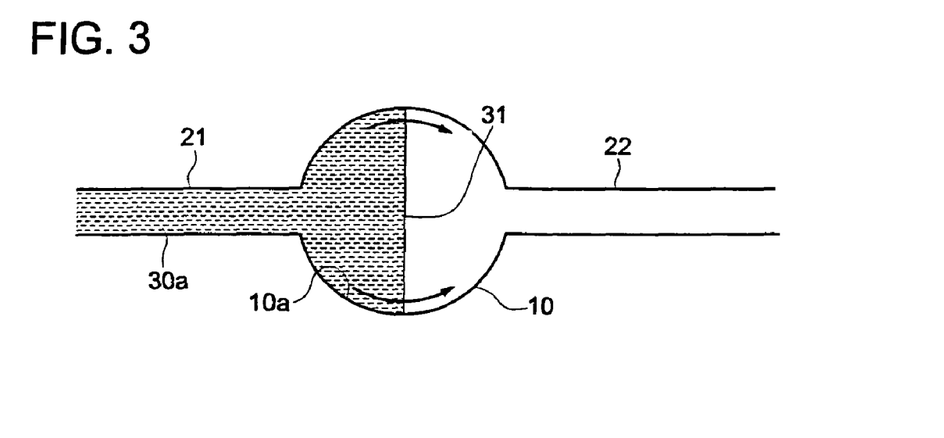
FIG. 3 is an explanatory drawing for the flowing of the first reagent into the reaction flow channel in which the reacting material is carried in the first embodiment of this invention.

When the front end 31 of the first reagent 30a is put into the reaction flow channel 10, as shown in FIG. 3, the peripheral portion of the gas-liquid interface in the front end 31 of the first reagent 30a passes in the forward direction on the wall surface of the reaction flow channel.

Figure 4:
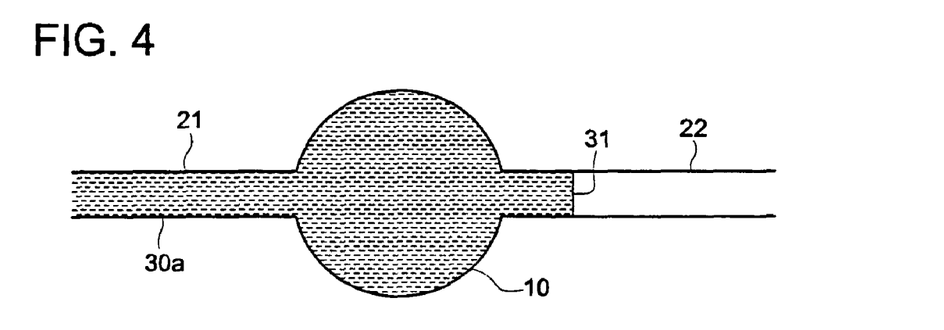
FIG. 4 is an explanatory drawing for the flowing of the first reagent into the reaction flow channel in which the reacting material is carried in the first embodiment of this invention.

When feeding of the first reagent 30a continues, as shown in FIG. 4, the front end 31 of the first reagent 30a passes through the reaction flow channel 10 and reaches to the flow channel 22 ahead of the flow channel 10.

Figure 5:
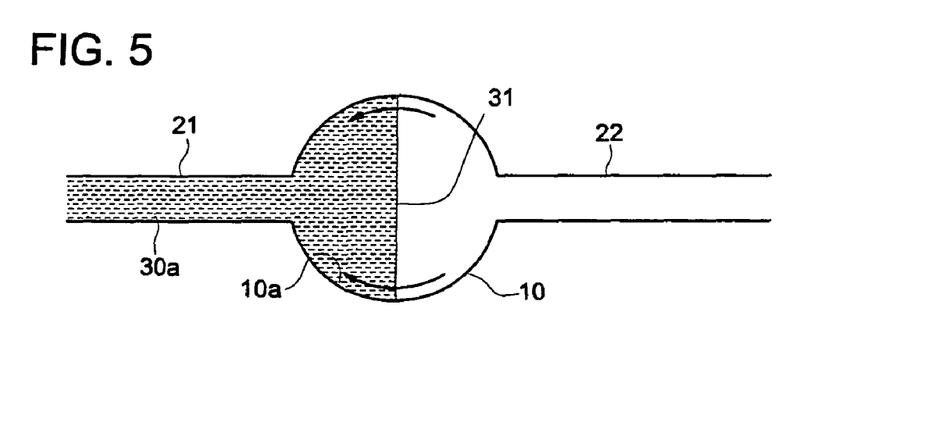
FIG. 5 is an explanatory drawing for the flowing of the first reagent into the reaction flow channel in which the reacting material is carried in the first embodiment of this invention.

In this manner, the reaction flow channel 10 is filled with first reagent 30a and then the first reagent 30a is flowed back in the reverse direction such that the front end 31 of the first reagent 30a is put into the reaction flow channel 10 again as shown in FIG. 5 and the peripheral portion of the gas-liquid interface at the front end 31 of the first reagent 30a passes in the reverse direction on the wall surface 10a of the reaction flow channel 10.

Subsequently, as same as shown in FIG. 3, the reagent is flowed once again from the state where the front end 31 of the first reagent 30a is positioned in the reaction flow channel 10 or in the upstream flow channel 21 of the reaction flow channel 10 so that the peripheral portion of the gas-liquid interface at the front end 31 passes through in the forward direction on the wall surface 10a of the reaction flow channel 10.

In this embodiment, the feeding operation is performed at least once, or preferably performed multiple times. Because the peripheral portion of the gas-liquid interface at the front end 31 of the first reagent 30a is moved back and forth and passes a plurality of times on the wall surface 10a of the reaction flow channel 10, movement of the fluid occurs on the wall surface 10a each time the first reagent 30a passes through and thus the situation where the first reagent 30a does not flow and constantly accumulates is prevented. As a result, new contact of the first reagent 30a with the reacting material that is carried on the wall surface 10a progresses and substitution of the reagent with the reacting material on the wall surface 10a is effectively performed. Thus the progress of the reaction is sped up.

Embodiment 2

FIG. 6-FIG. 9 are explanatory drawings for the flowing of the first and second reagent into the reaction flow channel on which the reacting material is carried in the second embodiment of this invention. It is to be noted that in these drawings, the structural elements which are the same as those in the first embodiment have been assigned the same numbers and descriptions thereof have been omitted.

In this embodiment, the operation is repeated in which the first reagent 30a is flowed into the reaction flow channel 10 and caused to react with the reacting material that is fixed on the flow channel wall and then the second reagent 30b is flowed into the reaction flow channel 10 and caused to react with the reacting material that is fixed on the flow channel wall.

Figure 6:
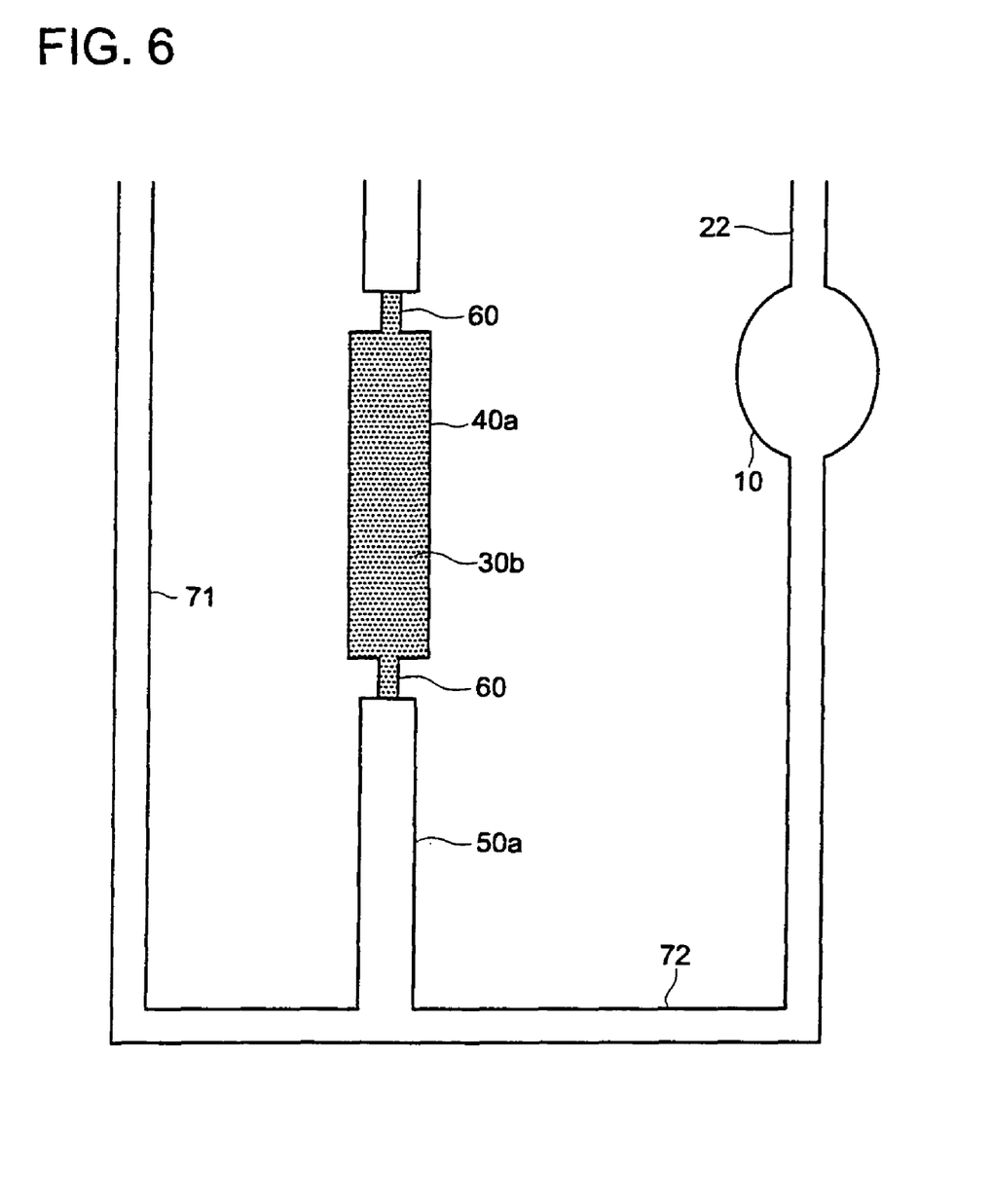
FIG. 6 is an explanatory drawing for the flowing of the first and second reagents into the reaction flow channel in which the reacting material is carried in the second embodiment of this invention.

As shown in FIG. 6, the second reagent 30b is stored in the reagent holding flow channel 40a. A water repellent valve 60 is provided respectively on the upstream end and the downstream end of the reagent holding flow channel 40a, and the second reagent 30b is held in the reagent holding flow channel 40a by these water repellent valves 60.

Figure 10:
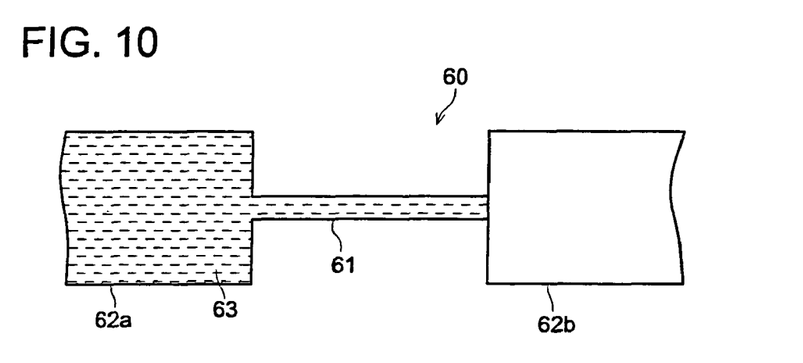
FIG. 10 is an exploded view of the water repellent valve.

FIG. 10 is an exploded view of the water repellent valve. The water repellent valve 60 in FIG. 10 comprises a flow control channel 61 which has a narrow flow channel width. The cross-sectional area (the cross-sectional area of a vertical cross-section of the flow channel) is smaller than that of the upstream flow channel 62a and the downstream flow channel 62b.

In the case where the flow channel wall is formed of a hydrophobic material such as resin and the like, passage into the downstream flow channel 62b of the fluid 63 that is in contact with the feed control channel 61 is controlled by the difference in surface tension with respect to the flow channel wall.

A flow fluid pressure exceeding a predetermined pressure is applied by the micropump in order to cause the fluid 63 to flow out to the downstream flow channel 62b, and as a result, the fluid 63 resists the surface tension and is expelled from the feed control flow channel 61 to the downstream flow channel 62. After the fluid 63 flows out to the flow channel 62b, even if the feed pressure required to expel the front end of the fluid 63 to the downstream flow channel 62b is not maintained, fluid flows to the downstream flow channel 62b.

That is to say, passage of the fluid forward from the feed control flow channel 61 is blocked until the feed pressure in the forward direction from the upstream side to the downstream side reaches a predetermined pressure, and by applying fluid feed pressure exceeding the predetermined pressure, fluid 63 passes through the feed control flow channel 61. One example is the case where feed control flow channel 61 is formed so the width by depth is 25 μm×25 μm for the flow channels 62a and 62b with width by depth of 150 μm×300 μm.

As shown in FIG. 6, a gas storage flow channel 50a is provided by intervening the water repellent valve 60 at the downstream side of the reagent holding flow channel 40a. The first reagent flow channel 71 merges with the gas storage flow channel 50a at the downstream end of the gas storage flow channel 50a, and the gas storage flow channel 50a, communicates with the common flow channel 72.

The following is a sequential description of the flowing operations when the first and the second reagents are caused to react with the reacting material. First, from the state shown in FIG. 6, the first reagent 30a is supplied from the reagent flow channel 71 to the reaction flow channel 10 through the common flow channel 72.

Figure 7:
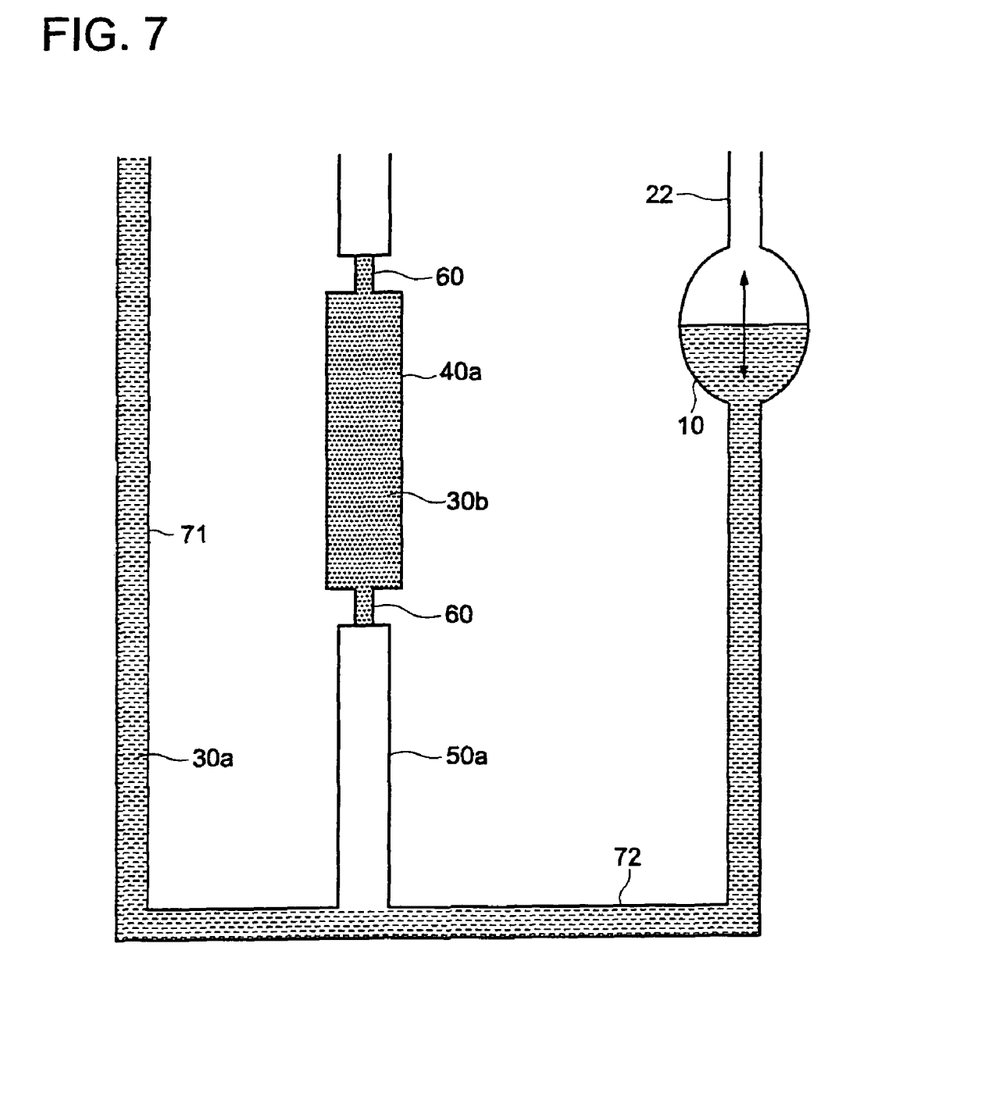
FIG. 7 is an explanatory drawing for the feeding of the first and second reagent into the reaction flow channel in which the reacting material is carried in the second embodiment of this invention.

Then, as shown in FIG. 7, after the front end of the first reagent 30a is moved into the reaction flow channel 10, in the same sequence as that of the first embodiment, the front end moves in the forward and reverse directions between the reaction flow channel 10 and the flow channel 22 ahead thereof. As a result, the peripheral portion of the gas-liquid interface in the front end of the first reagent 30a passes multiple times on the wall surface of the reaction flow channel 10 on which the reacting material is carried, and thus, new supply and contact of the first reagent 30a with the reacting material that is carried on the wall surface 10a progresses and the reaction is performed.

Figure 8:
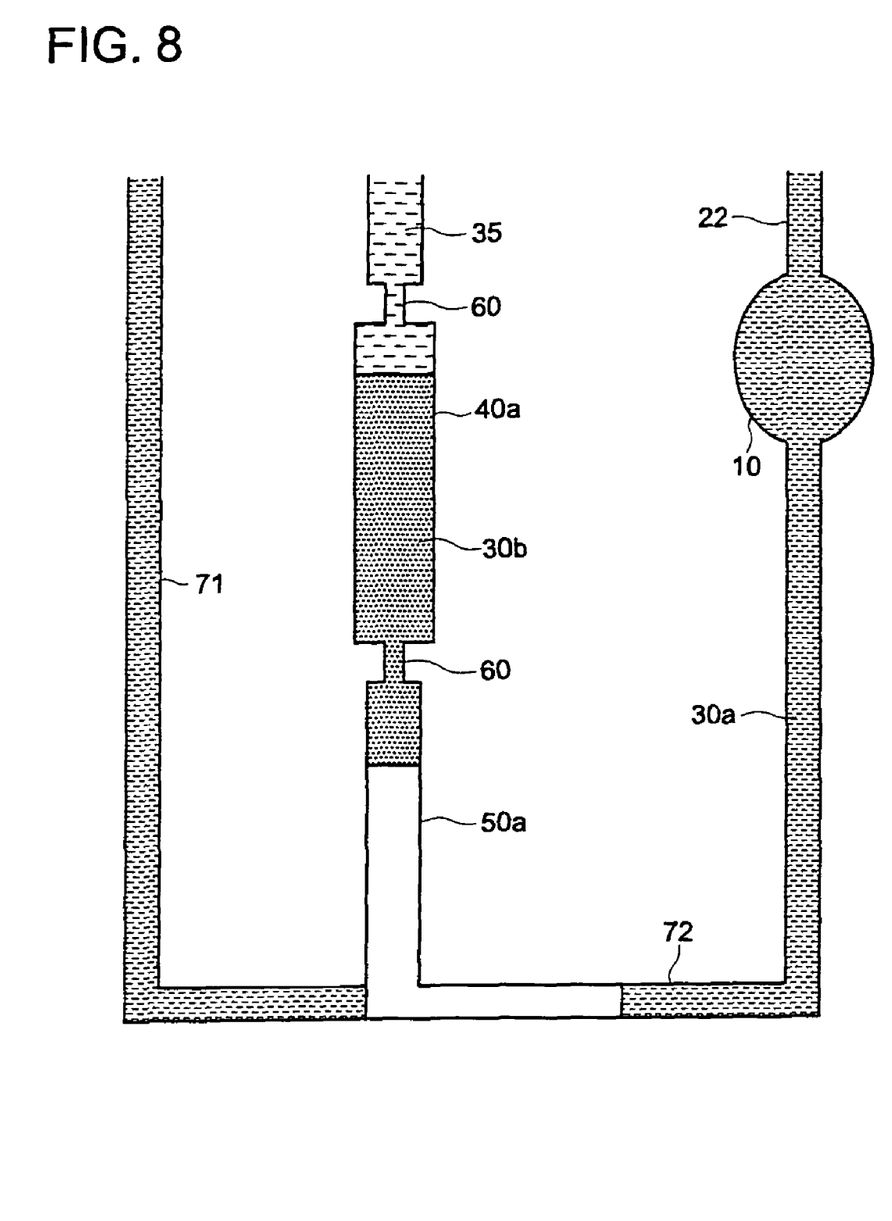
FIG. 8 is an explanatory drawing for the flowing of the first and second reagents into the reaction flow channel in which the reacting material is carried in the second embodiment of this invention.

Next as shown in FIG. 8, the second reagent 30b that is stored in the reagent holding flow channel 40a is expelled from the upstream side by the drive fluid 35 that is driven by the micropump (not shown) and pressure exceeding the fluid holding pressure of the water repellent valve 60 is applied and the second reagent 30b is expelled to the gas storage flow channel 50a. As a result, the gas that is stored in the gas storage flow channel 50a is pushed out to the common flow channel 72 side and the second reagent 30b is flowed to the reaction flow channel 10 in a state where the gas intervenes at the front end of the second reagent 3b.

Figure 9:
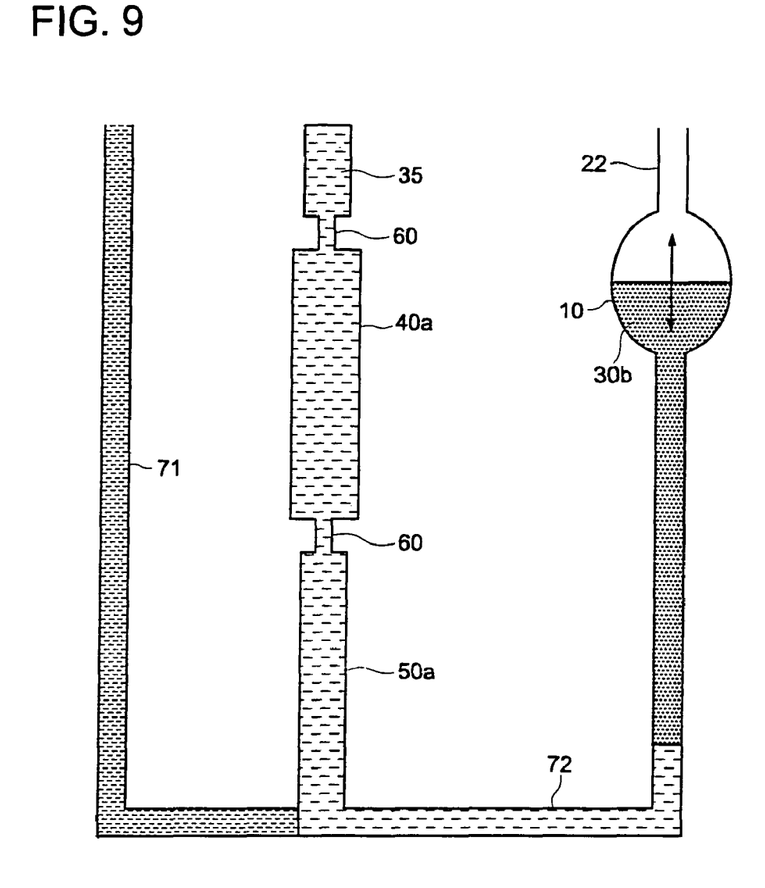
FIG. 9 is an explanatory drawing for the flowing of the first and second reagents into the reaction flow channel in which the reacting material is carried in the second embodiment of this invention.

As shown in FIG. 9, after the front end of the second reagent 30b is put into the reaction flow channel 10, in the same sequence as above, the front end moves in the forward and reverse direction between the reaction flow channel 10 and the flow channel 22 ahead thereof. This causes the peripheral portion of the gas-liquid interface at the front end of the second reagent 30b to pass multiple times on the wall surface of the reaction flow channel 10 which carries the reacting material. Thus, the reacting material carried on the wall surface reacts with the second reagent 30b while accelerating new supply and contact of the second reagent 30b with the reacting material.

As described above, this embodiment allows gas to intervene at the front end of the second reagent 30b, which can accelerate the reaction while moving back and forth the gas-liquid interface at the front end on the wall surface of the reaction flow channel 10, as the case with the first reagent 30a and the second reagent 30b.

Third Embodiment

Figure 11:
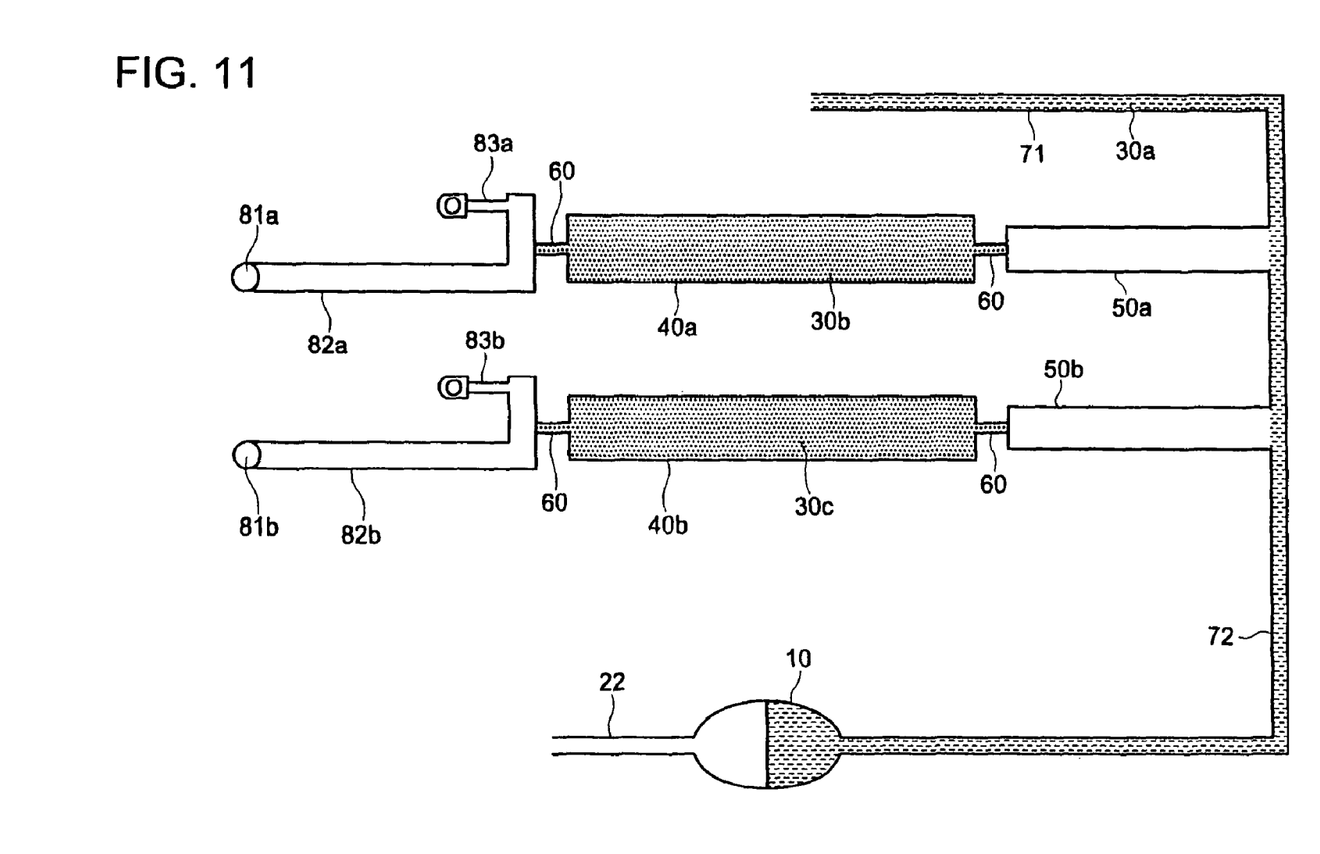
FIG. 11 is an explanatory drawing for the flowing of the first to third reagents into the reaction flow channel in which the reacting material is carried in the third embodiment of this invention.

FIG. 11 is an explanatory drawing for the flowing of the first to third reagents into the reaction flow channel on which the reacting material is carried in the third embodiment of this invention.

In FIG. 11, the structural elements which are the same as those in the above embodiments have been assigned the same numbers and descriptions thereof have been omitted.

In this embodiment, the first reagent 30a is flowed into the reaction flow channel 10 and caused to react with the reacting material that is fixed in the flow channel wall and then the second reagent 30b is flowed into the reaction flow channel 10 and caused to react with the reacting material that is fixed in the flow channel wall. After this the third reagent 30c is flowed into the reaction flow channel 10 and caused to react with the reacting material that is fixed in the flow channel wall.

As shown in FIG. 11, the second reagent 30b is stored in the reagent holding flow channel 40a and the third reagent 30c is stored in the reagent holding flow channel 40a. A water repellent valve 60 is provided on the upstream end and the downstream end respectively of the reagent holding flow channel 40a, and the second reagent 30b is held in the reagent holding flow channel 40a by these water repellent valves 60. Similarly, the third reagent 30c is held in the reagent holding flow channel 40b by two water repellent valves 60

A gas storage flow channel 50a is provided at the downstream side of the reagent holding flow channel 40a through the water repellent valve 60. The gas storage flow channel 50a merges with the first reagent flow channel 71 at the downstream end of the gas storage flow channel 50a and communicates with the common flow channel 72. Similarly, the gas storage flow channel 50b is provided at the downstream side of the reagent holding flow channel 40b through the water repellent valve 60. The gas storage flow channel 50b merges with the first reagent flow channel 71 at the downstream end of the gas storage flow channel 50b and communicates with the common flow channel 72.

The following is a description in sequence of the feeding operation when the first to third reagents are reacted with the reacting material. First, the first reagent 30a is supplied from the first reagent flow channel 71 to the reaction flow channel 10 through the common flow channel 72 and after the front end of the first reagent 30a is moved into the reaction flow channel 10, in the same sequence as that of the first embodiment, the front end moves in the forward and reverse directions between the reaction flow channel 10 and the flow channel 22 in the front thereof. This causes the peripheral portion of the gas-liquid interface at the front end of the first reagent 30a to pass multiple times on the wall surface of the reaction flow channel 10 which carries the reacting material. Thus, the reacting material carried on the wall surface reacts with the second reagent 30b while accelerating new supply and contact of the first reagent 30a with the reacting material.

Next, drive fluid is injected from the drive fluid injection port 81a in the chip that communicates with the micropump (not shown), the injection port being the opening provided upstream of the drive fluid flow channel 82a. The second reagent 30b that is stored in the reagent holding flow channel 40a is pushed from the upstream side and pressure exceeding the fluid holding pressure of the water repellent valve 60 is applied and the second reagent 30b is expelled to the downstream side. It is to be noted that 83a is a gas vent channel for removing gas bubbles between the drive fluid injected from the drive fluid injection port 81a and the second reagent 30b to the outside. More specifically, 83a is a narrow flow channel that controls the passage of fluid inside the flow channel due to water repellent property or high flow channel resistance and which has an end for removing gas bubbles from the inside of the flow channel to the outside.

As a result, the gas that is stored in the gas storage flow channel 50a is pushed out to the common flow channel 72 side and the second reagent 30b is fed to the reaction flow channel 10 in a state where the gas intervenes, at the second reagent 30b front end side. After the front end of the second reagent 30b is moved into the reaction flow channel 10, in the same sequence as above, the front end moves in the forward and reverse directions between the reaction flow channel 10 and the flow channel 22 ahead thereof. This causes the peripheral portion of the gas-liquid interface at the front end of the second reagent 30b to pass multiple times on the wall surface of the reaction flow channel 10 which carries the reacting material. Thus, the reacting material carried on the wall surface reacts with the second reagent 30b while accelerating new supply and contact of the second reagent 30b with the reacting material.

Next, drive fluid is injected from the drive fluid injection port 81b and the third reagent 30c that is stored in the reagent holding flow channel 40b is pushed from the upstream side and pressure exceeding the fluid holding pressure of the water repellent valve 60 is applied and the third reagent 30c is pushed out to the downstream side.

As a result, the gas that is stored in the gas storage flow channel 50a is expelled to the common flow channel 72 side and the third reagent 30c is flowed to the reaction flow channel 10 in a state where the gas intervenes at the third reagent 30c front end side. After the front end of the third reagent 30c is moved, into the reaction flow channel 10, in the same sequence as above, the front end moves in the forward and reverse directions between the reaction flow channel 10 and the flow channel 22 ahead thereof. This causes the peripheral portion of the gas-liquid interface at the front end of the second reagent 30b to pass multiple times on the wall surface of the reaction flow channel 10 which carries the reacting material. Thus, the reacting material carried on the wall surface reacts with the third reagent 30c while, accelerating new supply and contact of the third reagent 30c with the reacting material.

As described above, when the first to third reagents are flowed to the reaction flow channels, gas is allowed to intervene, thus making it possible to accelerate the reaction of these regents with the reacting material while moving back and forth the gas-liquid interface at the front end of the reaction flow channel 10 on the wall surface of the reaction flow channel 10.

Figure 12:
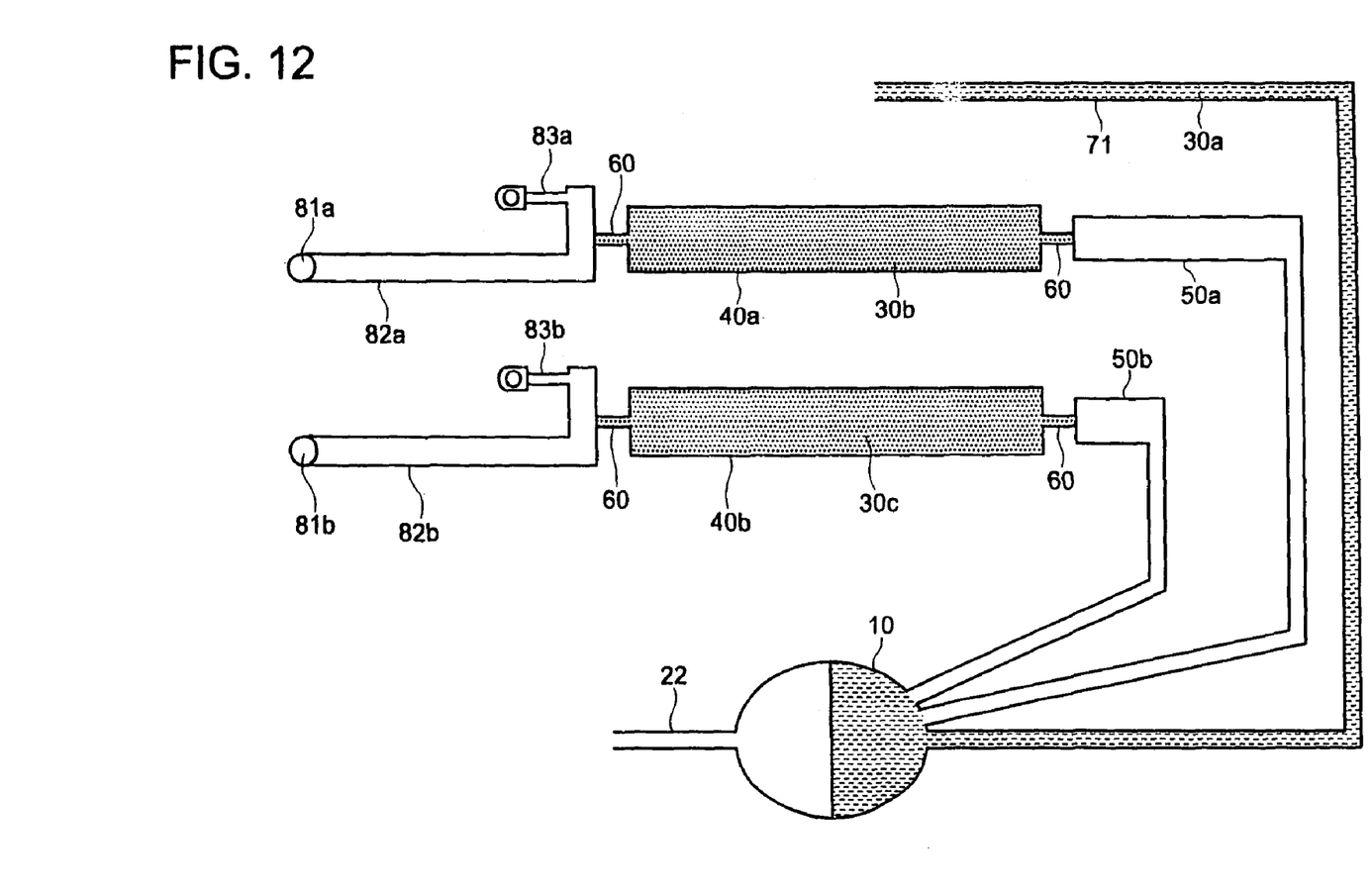
FIG. 12 shows the flow channel for describing the modified example of the third embodiment.

FIG. 12 shows the flow channel for describing the modified example of the third embodiment. In this modified example, the common flow channel 72 is not provided as in FIG. 11 and the gas storage flow channels 50a and 50b are directly connected to the reaction flow channels respectively. Even when the flow channel is structured in this manner, the feeding operation is performed in the same manner as described in the third embodiment, and the first to third reagents are flowed to the reaction flow channel 10 in a state where the gas intervenes at each front end of the first to third reagents. This can accelerate the reaction by passing multi times the peripheral portion of the gas-liquid interface on the wall surface of the reaction flow channel 10 in which the reacting material is fixed.

The invention has been described based on these embodiments, but the invention is not to be limited by these embodiments, and various changes and modifications are possible provided that they do not depart from the scope of the invention.

For example, by configuring the flow channel 22 as a closed airtight space from the point of the reaction flow channel 10 forward, reagent is flowed to the reaction flow channel 10 by the fluid feeding micropump and then, the reagent returns to the reaction flow channel 10 side when pressure falls due to the driving of the micropump being stopped, because the gas space inside the flow channel 22 is compressed by the reagent. As a result, the flow channel 22 with the closed end acts as a damper and the reagent is able to move back and forth inside the reaction flow channel 10.

In this case, the gas vent channel 83a (83b) is preferably provided at a position before of the reaction flow channel 10 as shown in FIG. 11. By providing this gas vent channel, after the reagent is pressure-flowed to the reaction flow channel 10 using the micropump for flowing fluid, by stopping the micropump, the reagent returns to the reaction flow channel 10 side and the front end of the reagent returns to the position of the gas vent channel where the gas is vented to the atmosphere because the gas space in the flow channel 22 described above is compressed by the reagent. As a result, the complex control of the micropump is not necessary and the reagent can easily move back and forth inside the reaction flow channel 10.

The invention claimed is:

1. A reaction method for performing a reaction in a reaction flow channel of a microchip, the microchip including (i) the reaction flow channel, wherein a reacting material is fixed on an inner wall surface of the reaction flow channel, (ii) a first flow channel connected upstream of the reaction flow channel, wherein a gas is stored in the first flow channel, and (iii) a second flow channel connected downstream of the reaction flow channel, and the reaction method comprising:
   flowing a first reagent liquid into the second flow channel through the first flow channel and the reaction flow channel in a forward direction, whereby a peripheral portion of a gas-liquid interface at a front end of the first reagent liquid passes along the inner wall surface of the reaction flow channel in the forward direction;
   flowing back the first reagent liquid into the first flow channel through the reaction flow channel in a reverse direction, whereby the peripheral portion passes along the inner wall surface of the reaction flow channel in the reverse direction; and
   flowing the first reagent liquid into the second flow channel through the reaction channel again in the forward direction, whereby the peripheral portion once again passes along the inner wall surface of the reaction flow channel in the forward direction,
   wherein the reaction is performed by contacting the first reagent liquid with the reaction material fixed on the inner wall surface of the reaction flow channel.

2. The reaction method according to claim 1, further comprising performing, after the reaction between the first reagent liquid and the reacting material has been performed:
   flowing a second reagent liquid to react with the reacting material fixed on the inner wall surface of the reaction flow channel into the reaction flow channel with intervening gas at a front end of the second reagent liquid; and
   flowing the second reagent liquid such that a peripheral portion of a gas-liquid interface at the front end of the second reagent liquid moves back and forth on the inner wall surface of the reaction flow channel,
   whereby a reaction between the second reagent liquid and the reacting material is performed.

3. The reaction method according to claim 2, wherein the microchip further comprises:
   a reagent holding flow channel which stores the second reagent liquid, wherein the reagent folding flow channel is connected upstream of the reaction flow channel;
   a gas storage flow channel which stores gas, wherein the gas storage flow channel is disposed at a downstream side of the reagent holding flow channel and communicates with the reaction flow channel directly or indirectly at downstream side of the gas storage flow channel; and
   a water repellent valve which intervenes between a downstream end of the reagent holding flow channel and an upstream end of the gas storage flow channel and includes a flow control path that has a smaller cross-sectional area than the reagent holding flow channel and gas storage flow channel, wherein the water repellent valve passes the second reagent liquid forward from the reagent holding flow channel when a flow fluid pressure larger than a predetermined pressure is applied from an upstream side, and
   wherein, after the reaction between the first reagent liquid and the reacting material is performed, the reaction between the second reagent liquid and the reacting material is performed by:
   pushing the second reagent liquid stored in the reagent holding flow channel forward from the reagent holding flow channel through the water repellent valve to downstream of the reagent holding flow channel;
   flowing the second reagent liquid into the reaction flow channel with the gas stored in the gas storage flow channel as the gas intervening at the front end of the second reagent liquid; and
   flowing the second reagent liquid such that the peripheral portion of the gas-liquid interface at the front end of the second reagent liquid moves back and forth on the wall surface of the reaction flow channel.

4. The reaction method according to claim 1, wherein the second flow channel downstream of the reaction flow channel forms a closed air tight space and the peripheral portion of the gas-liquid interface at the front end of the first reagent liquid moves back and forth on the inner wall surface of the reaction flow channel by reducing a pressure from outside after flowing the first reagent liquid into the reaction flow channel by the pressure.

5. The reaction method according to claim 4, wherein a volume of the second flow channel downstream of the reaction flow channel is larger than a volume of the reaction flow channel.

6. The reaction method according to claim 4, wherein the microchip further comprises a gas vent channel which has an end opened to an outer atmosphere and which is provided at a position upstream of the reaction flow channel.

7. The reaction method according to claim 1, wherein flowing back the first reagent liquid into the first flow channel through the reaction flow channel in the reverse direction and flowing the first reagent liquid into the second flow channel through the reaction channel again in the forward direction are performed a plurality of times.

* * * * *